(12) United States Patent
Potter

(10) Patent No.: US 6,971,260 B2
(45) Date of Patent: Dec. 6, 2005

(54) OVERBURDEN ROCK CORE SAMPLE CONTAINMENT SYSTEM

(75) Inventor: Jared M. Potter, San Carlos, CA (US)

(73) Assignee: Coretest Systems, Inc., San Jose, CA (US)

( * ) Notice: Subject to any disclaimer, the term of this patent is extended or adjusted under 35 U.S.C. 154(b) by 0 days.

(21) Appl. No.: 10/757,111

(22) Filed: Jan. 13, 2004

(65) Prior Publication Data

US 2005/0150273 A1  Jul. 14, 2005

(51) Int. Cl.[7] .......................... G01N 15/08; E21B 49/00
(52) U.S. Cl. ....................................... 73/38; 73/152.05
(58) Field of Search .............................. 73/38, 152.05, 73/152.06, 152.07, 152.08, 152.09, 152.11; 494/45

(56) References Cited

U.S. PATENT DOCUMENTS

| | | | |
|---|---|---|---|
| 2,534,718 A * | 12/1950 | Leas et al. .................... | 73/38 |
| 2,713,789 A * | 7/1955 | Kelton ........................... | 73/38 |
| 3,023,606 A * | 3/1962 | Sarem ........................... | 73/38 |
| 4,495,795 A * | 1/1985 | Gupta ........................... | 73/38 |
| 4,531,404 A * | 7/1985 | Phelps et al. ................. | 73/38 |
| 4,567,373 A | 1/1986 | O'Meara, Jr. et al. | |
| 4,649,737 A * | 3/1987 | Jones ........................... | 73/38 |
| 4,740,077 A | 4/1988 | Goodwill | |
| 4,817,423 A | 4/1989 | Christiansen | |
| 5,328,440 A | 7/1994 | Chen et al. | |
| 5,351,525 A | 10/1994 | Ragazzini et al. | |
| 5,442,950 A * | 8/1995 | Unalmiser et al. ............ | 73/38 |
| 5,563,333 A * | 10/1996 | Haines et al. ................. | 73/38 |
| 5,719,327 A * | 2/1998 | Maini et al. .................. | 73/38 |
| 6,185,985 B1 | 2/2001 | Fleury et al. | |
| 6,415,649 B1 | 7/2002 | Spinler et al. | |
| 6,490,531 B1 | 12/2002 | Goglin et al. | |

* cited by examiner

Primary Examiner—Michael Cygan
(74) Attorney, Agent, or Firm—Townsend and Townsend and Crew, LLP

(57) ABSTRACT

A compression cell for rock or soil core samples applies and restores lithostatic or overburden pressure to core samples extracted from wells drilled deep into the earth. A method of applying lithostatic pressure to a core sample is disclosed along with the apparatus which effects the application. The cell construction that maintains the litho static pressure and the process of utilizing the cell and sample under essentially deep earth ambient conditions are set forth.

7 Claims, 3 Drawing Sheets

OVERBURDEN ROCK CORE SAMPLE CONTAINMENT SYSTEM

CROSS-REFERENCES TO RELATED APPLICATIONS

Not applicable

STATEMENT AS TO RIGHTS TO INVENTIONS MADE UNDER

FEDERALLY SPONSORED RESEARCH OR DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

This invention relates to a compression cell for soil or rock core samples for applying and restoring lithostatic or overburden pressure to soil or rock core samples extracted from wells drilled deep into the earth. Specifically, a method of applying lithostatic pressure to a core sample is disclosed along with the apparatus which effects the application. The cell which maintains the litho static pressure and the process of utilizing the cell and sample under essentially deep earth ambient conditions are set forth.

BACKGROUND OF THE INVENTION

Underground rock pressures and underground fluid pressures differ radically. Underground rock pressures relate directly to overburden in and around the particular soil sample being tested. For example, in certain rock conditions where a sample is at a depth of about 10,000 feet, overburden pressures in the range to 8000 to 10,000 pounds per square inch may be experienced. Underground fluid pressures differ radically. As the soil usually defines paths through which fluid can flow, the fluid pressure is usually independent of the rock pressure. Taking the example of the core sample at 10,000 feet, and remembering the fluids have a density about one third of that of a rock, pressures in the range of 3000 to 4000 pounds per square inch may be present.

Core samples are frequently extracted from deeply drilled the wells so that fluid flow properties within the rock of the core may be analyzed. Pore size, flow properties, capillary pressure and the like are all dependent upon the overburden pressure or lithostatic pressure upon a rock sample. If accurate testing of such core samples is to occur, the lithostatic pressures must be re-created.

It is also known that the deeper one goes into the earth's mantle, the greater the temperature present in the ambient rock. Accordingly, if testing under the ambient conditions is to be re-created, it must be done under the same thermal conditions as well as lithostatic conditions as existed for the sample at its original depth within the earth.

It is known to use centrifuges in the analysis of such core samples. See for example O'Meara Jr. et al. U.S. Pat. No. 4,567,373, Goodwill U.S. Pat. No. 4,740,077, Christiansen U.S. Pat. No. 4,817,423, Chen et al. U.S. Pat. No. 5,328,440, Ragazzini et al. U.S. Pat. No. 5,351,525, Spinler et al. U.S. Pat. No. 6,415,649, Fleury et al. U.S. Pat. No. 6,185,985, and Goglin et al. U.S. Pat. No. 6,490,531. In none of these references is litho static pressure created independently of fluid pressure.

Discovery

I have come to the realization that for the realistic testing of drill core samples, at least the litho static pressures must be re-created on the sample before accurate testing can occur. Preferably, I re-create both litho static pressures and thermal temperatures before testing. Only after both the litho static and thermal ambient are re-created, is it possible to conduct accurate testing.

BRIEF SUMMARY OF THE INVENTION

A process for loading a centrifuge rotor with overburden pressure or lithostatic pressure onto a rock core sample is disclosed. A titanium containment cylinder closed at one end forms the compression cell. A rubber liner closing one end of the containment cylinder also covers the sides of the containment cylinder. A core sample is placed interior of the liner so that the liner is between the containment cylinder and the core sample. A loading ring is utilized to compress the rubber liner within the containment cylinder over the placed core sample to uniformly compress the rubber liner and as a result the core sample from both ends as well as the cylindrical sides. Compression of the loading ring occurs so that the rubber liner essentially acts as a fluid to apply lithostatic pressure to the core sample uniformly on all sides. Provision is made to heat the core sample to ambient earth temperatures, preferably before compression occurs. A hydraulic press for applying the overburden or lithostatic pressure to the core sample is disclosed. Fluid inlet/outlets communicate through both ends of the containment cylinder to enable fluid measurements to be taken of the compressed core sample. The cell finds preferred use within a centrifuge or can be used independently for measurement of core sample fluid properties. Fluid, typically oil, gas, water, brine, or mixtures thereof, is passed through the core sample to determine hydrodynamic and hydrostatic characteristics of the rock core sample at the lithostatic temperature and pressure.

DETAILED DESCRIPTION OF THE INVENTION

Figure 1:
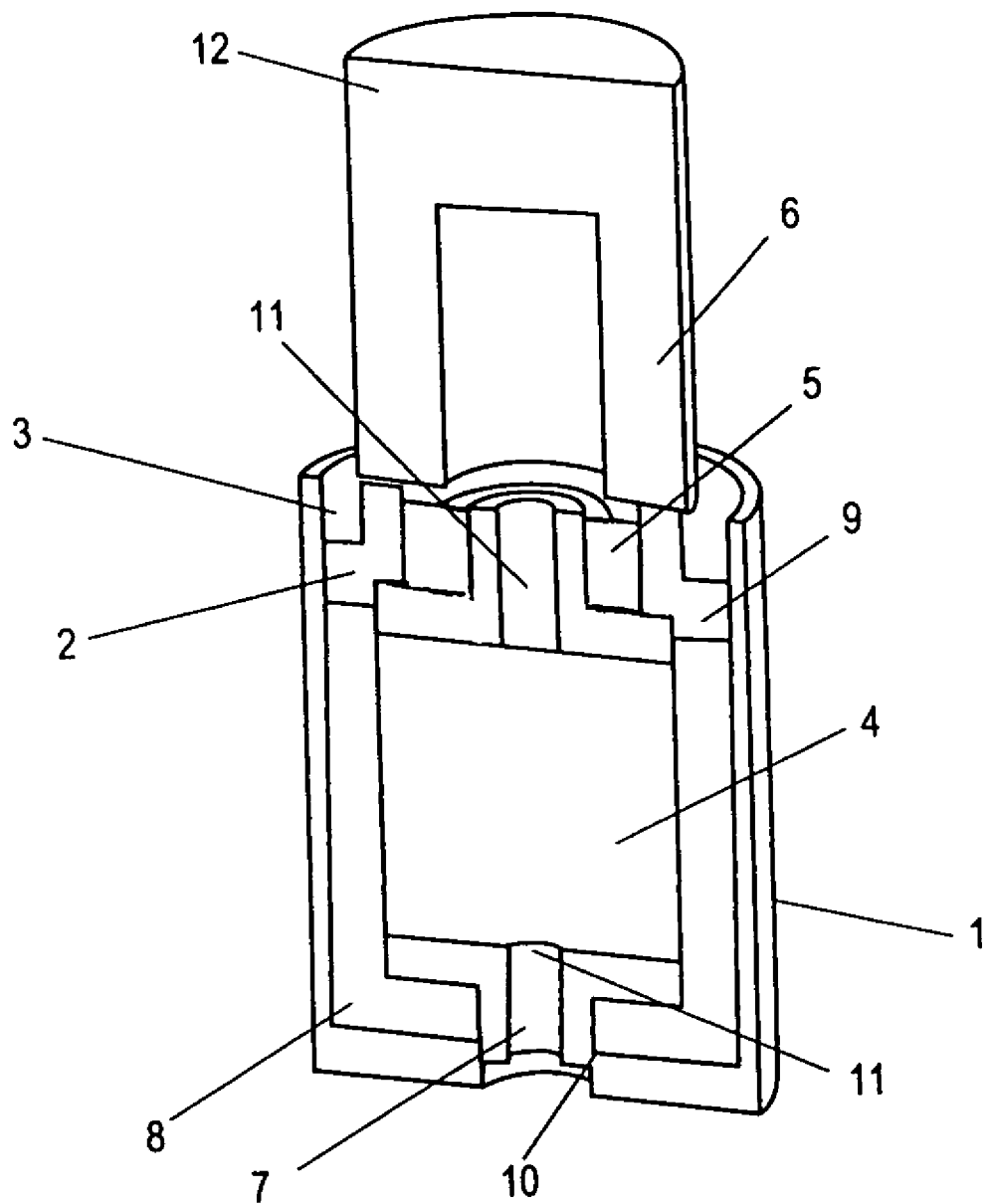
FIG. 1 is a perspective view in cross-section of a cell according to this invention illustrating an extracted core sample being compressed by a removable loading fixture with the rubber sleeve a centrally acting as a fluid for causing compression between the outer body of the containment cell and the inner and contained core sample.

Referring to FIG. 1, an overburden cell C is illustrated. Cell C is composed of an metal outer body 1 with rubber sleeve 8 containing rock core 4. Metal outer body 1 is cylindrical, closed at one end and an open at the opposite end. Lower and upper metal end plugs 6, 7 which are equipped with fluid inlet/outlet ports 11 are within the interior of outer metal body 1. The reader will appreciate that the inlet/outlet ports 11 are typically larger than the largest particle size of the rock core sample 4. Typically, when overburden pressures are applied, the solids form a compression dome over the port 11 which allows substantially unimpeded fluid communication into and out of cell C.

A push ring 2 at the open end of metal outer body 1 is used to compress the rubber sleeve when placed within a loading press. Rubber sleeve 8 acts essentially as a fluid on all sides and one end of rock core 4. It applies the requisite overburden pressure on to rock core 4. Specifically, removable loading fixture 12 acts on push ring 2 to apply compression to rubber sleeve 8.

When pressure is applied to rubber sleeve 8 and rock core 4, locking closure 3 is screwed in after push ring 2 maintaining the pressure on the push ring. The axial loading nut (5) is adjusted prior to pressurizing to adjust for minor changes in rock core length.

Anti-extrusion rings 9, 10 prevent the pressurized rubber sleeve from flowing into the opening between the outer body 1 and the end plugs 6, 7 when pressure is applied. The result is that rock core 4 as overburden pressure applied by rubber sleeve 8. By the expedient of adjusting the locking closure 3, the overburden or lithostatic pressure can be preserved on rock core 4.

Figure 2:
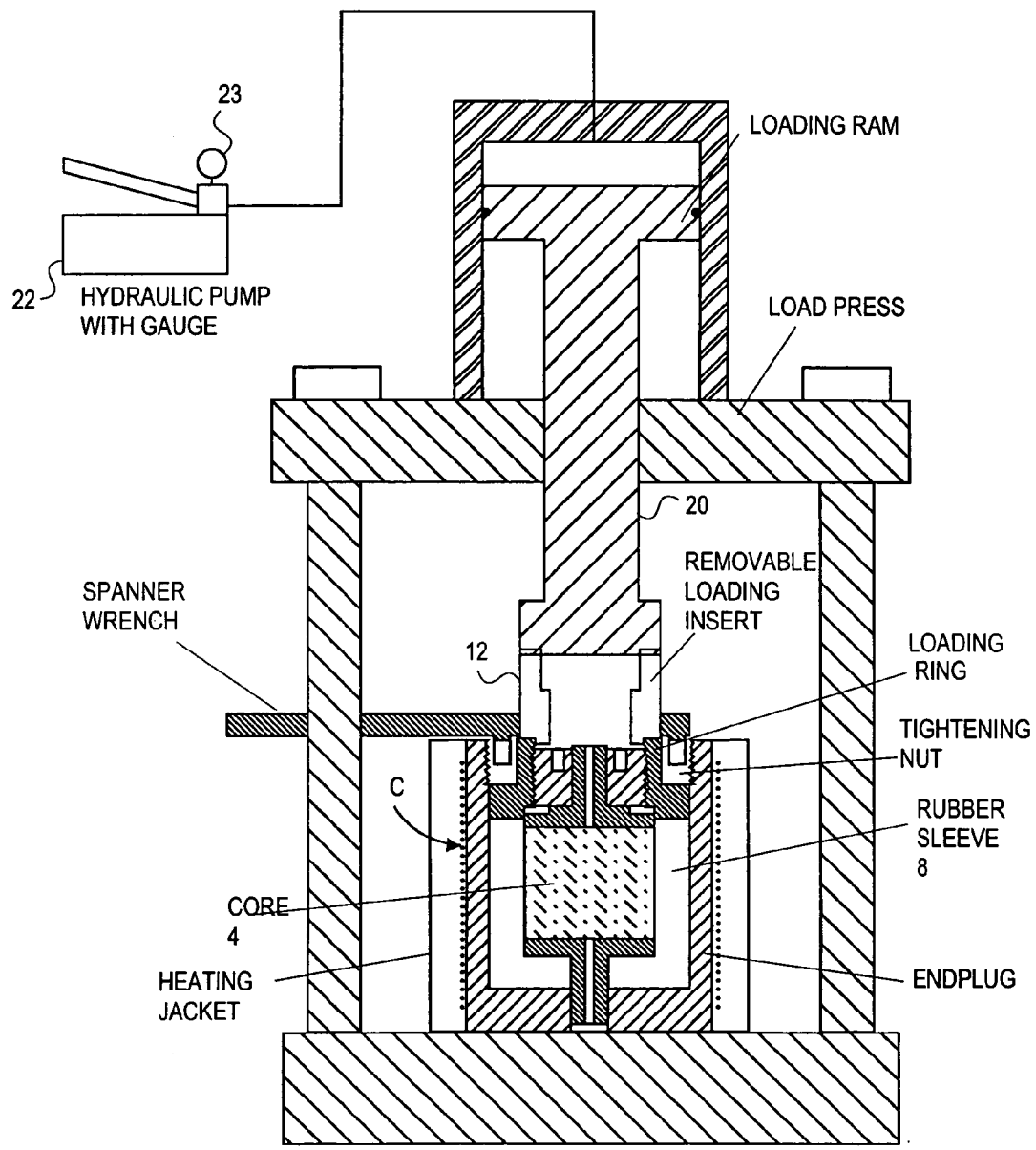
FIG. 2 is a sectional view of the cell of FIG. 1 placed within a hydraulic press for applying or releasing the overburden or lithostatic stress on the core sample; and, FIG. 3 is a schematic of the cell according to this invention being utilized within the centrifuge.

Referring to FIG. 2, overburden cell C a shown placed within the heating jacket J. Typically, heating jacket J is raised to a temperature ambient to that of the rock core 4 at the depth from which it is originally extracted. Thereafter, the overburden pressure is applied by having a loading ram 20, actuated by hydraulic pump 22 with gauge 23. Pressure is applied through loading ram 21 to removable loading fixture 12. Rubber sleeve 8 becomes fluid like and applies to rock core 4 the requisite overburden or lithostatic pressure. It will then be understood, that the core sample 4 is loaded with ambient overburden pressure and because of the heating previously described will also reside at ambient temperature. The reader will understand that upon cooling, cell. C will relieve some of the pressure on rock core 4. By the simple expedient of reheating the cell C, both the ambient temperature and lithostatic pressure can be restored.

During loading of stress on rubber sleeve 8, it is important to pre-heat the sample and sleeve assembly to the temperature at which the test will be conducted. The pressurizing system should be left at conditions for a period of time to allow for some plastic flow of the sleeve into small voids and openings prior to locking in the rings and removing the system from the press. To remove the sample from the chamber it is necessary to re-apply the same stress to the rubber sleeve in order to unscrew the retaining ring.

Figure 3:
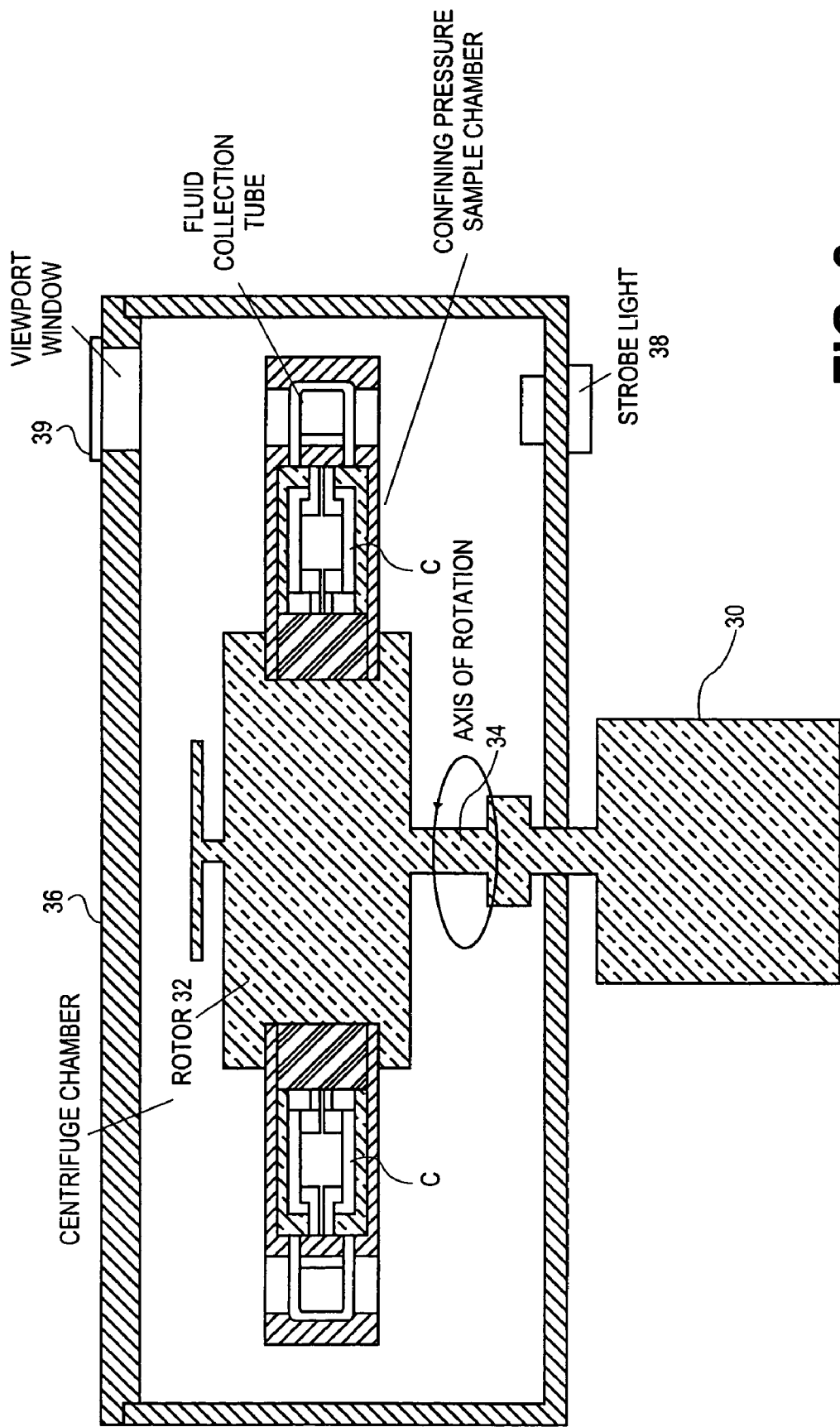

The primary uses of the cell here disclosed is in a centrifuge. Referring to FIG. 3, a centrifuge is schematically described in which a motor 30 drives rotor 32 about axis of rotation 34. Here, two cells C are shown undergoing centrifugation with in centrifuge chamber 36. Real-time fluid volume changes can be measured through the respective cells C by strobe light 38 through view port window 39.

It will be just as well understood that the cell C can be utilized without placement into a centrifuge. Specifically, rock core 4 can either have fluid placed under static conditions within it or alternatively have fluid ambient to the rock core 4 removed from the core by a displacing fluid.

From the above specification, it will be understood that I disclose at least four separate areas of utility. First, I have realized that overburden or lithostatic pressure is substantially independent of hydrostatic pressure. This being the case, I disclose a process of placing lithostatic pressure (and even temperature) on a sample first and then measuring its fluid flow characteristics second.

secondly, I utilize the rubber liner within my containment cell surrounding the core sample. This rubber liner acts essentially as a fluid and is able to uniformly impose on the core sample the ambient lithostatic pressure that the core sample has in its natural environment. Thus when fluid flow characteristics are measured, they can be measured at the original lithostatic pressure. It is also to be noted, that by preheating the core sample to the temperature found at its original depth within the earth, I can more or less completely emulate the conditions under which the core sample was extracted in the first instance. There are certain hysteresis effects which result from the cycling of temperatures and pressures on a rock core sample. These I cannot completely eliminate. However, by the following the disclosed testing routine, these effects can be minimized.

Thirdly, I disclose an article. Simply stated, the cell without with the lithostatically loaded specimen is a useful article of commerce.

Finally, the cell combined with a hydraulic press is a patentable article.

What is claimed is:

1. A process for loading a centrifuge rotor with overburden onto a contained rock core sample comprising the steps of:
    providing a containment cylinder closed at one end with a fluid inlet/outlet through the closed end of the containment cylinder;
    providing a rubber liner covering the sides of the containment cylinder and closing one end of the containment cylinder around the inlet/outlet;
    placing core sample interior of the liner and containment cylinder for compression by the rubber liner;
    providing a loading ring for compressing the rubber liner within the containment cylinder over the placed core sample; and,
    compressing the loading ring so that the rubber liner essentially reacts as a fluid to apply overburden pressure to the core sample.

2. The process for loading a centrifuge rotor with overburden onto a contained rock core sample according to claim 1 and including the further steps of:
    providing a locking mechanism connected between the loading ring and the containment cylinder for maintaining the loading ring compression on the rubber liner; and,
    locking the locking mechanism after the compressing step to statically maintained the overburden pressure on the core sample.

3. The process for loading a centrifuge rotor with overburden onto a contained rock core sample according to claim 1 and wherein the passing fluid through the core samples step includes:
    placing the containment cylinder in a centrifuge.

4. The process for loading a centrifuge rotor with overburden onto a contained rock core sample according to claim 1 and wherein the passing fluid through the core samples step includes:
    passing fluid from one inlet/outlet to the other inlet/outlet through core sample.

5. A chamber for containing a core sample with overburden pressure comprising:
    a containment cylinder closed at one end;
    a fluid inlet/outlet through the closed end of the containment cylinder;

a rubber liner covering the sides of the containment cylinder and closing one end of the containment cylinder around the inlet/outlet;

a core sample interior of the liner and containment cylinder for compression by the rubber liner;

a loading ring for compressing the rubber liner within the containment cylinder over the placed core sample, a fluid inlet/outlet through the loading ring;

means compressing the loading ring so that the rubber liner essentially reacts as a fluid to apply lithostatic pressure to the core sample.

6. A process for loading a cell contained rock core sample with overburden pressure comprising the steps of:

providing a containment cylinder closed at one end;

providing a fluid inlet/outlet through the closed end of the containment cylinder;

providing a rubber liner around the inlet/outlet covering the sides of the containment cylinder and closing one end of the containment cylinder;

placing core sample interior of the liner and containment cylinder for compression by the rubber liner;

providing a loading ring for compressing the rubber liner within the containment cylinder over the placed core sample, providing a fluid inlet/outlet through the loading ring;

compressing the loading ring in an hydraulic press so that the rubber liner essentially reacts as a fluid to apply lithostatic pressure to the core sample; and, passing fluid through the core sample to determine fluid flow characteristics of the sample at the lithostatic pressure.

7. The process according to claim 6 comprising the further step of:

before the compressing step, heating the containment cylinder, rubber liner, and core sample to a temperature ambient to the rock core sample with overburden within its natural environment.

* * * * *